(12) United States Patent
Netke et al.

(10) Patent No.: US 8,012,935 B2
(45) Date of Patent: Sep. 6, 2011

(54) SYNTHETIC PEPTIDES AND METHODS FOR TREATING CANCER INVASION AND METASTASIS

(75) Inventors: Shrirang Netke, San Bruno, CA (US); Aleksandra Niedzwiecki, San Jose, CA (US); Matthias Rath, Bocholtz (NL)

(73) Assignee: Matthias W. Rath, Aptos, CA (US)

( * ) Notice: Subject to any disclaimer, the term of this patent is extended or adjusted under 35 U.S.C. 154(b) by 0 days.

(21) Appl. No.: 10/350,258

(22) Filed: Jan. 23, 2003

(65) Prior Publication Data

US 2003/0139345 A1 Jul. 24, 2003

Related U.S. Application Data

(60) Provisional application No. 60/351,317, filed on Jan. 23, 2002.

(51) Int. Cl.
*A61K 38/10* (2006.01)
(52) U.S. Cl. ............... 514/16; 530/300; 530/328; 514/2
(58) Field of Classification Search ............... 514/2, 16; 530/300, 328
See application file for complete search history.

(56) References Cited

U.S. PATENT DOCUMENTS 5,585,356 A * 12/1996 Liotta et al. .............. 514/17
5,646,027 A * 7/1997 Ye et al. .................. 435/219

FOREIGN PATENT DOCUMENTS

| WO | WO 90/01228 A | * | 9/1990 |
| WO | WO90/10228 | | 9/1990 |
| WO | WO01/31019 | | 5/2001 |

OTHER PUBLICATIONS

Zalutsky (J. Nucl. Med. Jan. 2005; 46 (Suppl. 1): 151S-156S).*
Prasad et al. (Curr. Med. Chem. Anti-Canc. Agents. Jul. 2004; 4 (4): 347-361).*
Kemper et al., (Cancer Treat. Rev. Aug. 2004; 30 (5): 415-423).*
Gura (Science. 1997; 278: 1041-1042).*
Saijo et al. (Cancer Sci. Oct. 2004; 95 (10): 772-776).*
Kelland (Eur. J. Cancer. Apr. 2004; 40 (6): 827-836).*
Bergers et al. (Current Opinion in Genetics and Development. 2000; 10: 120-127).*
Koivunen E. et al. "Tumor targeting with a selective gelatinase inhibitor", Nature Biotechnology: 17(8) Aug. 1999, pp. 768-774.

* cited by examiner

*Primary Examiner* — Stephen L Rawlings
(74) *Attorney, Agent, or Firm* — Geeta Kadambi Riddhi IP LLC (57) ABSTRACT

The present invention relates to synthetic oligopeptides that exhibit inhibitory activity towards cancer invasion and metastasis. The peptides of the invention comprise PRKPK-WDK (SEQ ID:2) peptide corresponding to amino acids of 85 to 92 of the matrix metalloproteinase (MMP-2), and fragments, analogs and homologs. The invention also relates to the uses of such peptides as inhibitory of human cancer invasion and metastasis and further to their therapeutic use in preventing and treating other pathological conditions related to the degradation of extracellular matrix by MMPs.

2 Claims, 4 Drawing Sheets

Figure 1: Amino Acid Sequence of the Enzyme MMP2.
The sequences selected have been boxed for ease in identification.

Figure 2: Comparative Inhibitory Activities of Selected Oligopeptides Sequences in MMP2.
II, PRKPKWDK; III, EDYDRDKKY; IV, GRSDGLM; V, NYDDDRKW;
VI, LPPDVQRVD; VII, RYNEVKKKMDP. Ref: TMRKPRCGNPDVAN Figure 3: Inhibitory Effect of polypeptide PRKPKWDK on Matrigel Invasion and Migration by Human Melanoma Cells A2058

Figure 4: Inhibitory Effect of Oligopeptide PRKPKWDK on Matrigel Invasion and Migration by Human Breast Cancer Cells MCF7

SYNTHETIC PEPTIDES AND METHODS FOR TREATING CANCER INVASION AND METASTASIS

CROSS-REFERENCE TO RELATED APPLICATION

This application claims the benefit under 35 U.S.C. § 119 (e) of U.S. provisional application Serial No. 60/351,317 filed Jan. 23, 2002, the content of which is incorporated herein by reference in its entirety.

FIELD OF THE INVENTION

The present invention relates to synthetic oligopeptides that exhibit inhibitory activity towards cancer invasion and metastasis. The synthetic oligopeptides of the invention comprise PRKPKWDK (SEQ ID: 2) peptide corresponding to amino acids 85 to 92 of the matrix metalloproteinase-2 (MMP-2), and fragments, analogs and homologs. The invention also relates to a formulation comprising such synthetic oligopeptides in preventing and treating human cancer invasion and metastasis and further to the therapeutic use of the formulation in preventing and treating cancer and other pathological conditions related to the degradation of extracellular matrix by matrix metalloproteinases (MMPs).

BACKGROUND OF THE INVENTION

A variety of pathological conditions including neoplastic diseases are associated with an increased activity of MMPs. MMPs are a group of serine proteinases that can degrade the extracellular matrix (ECM). MMP are secreted in the extracellular matrix in their zymogen form. Upon activation, MMP enzymatic activity becomes active and digest ECM, a process known to play a major role in cancer metastasis.

They are at least a few members of proteinases within the MMP family, and they include MMP-1, MMP-2, MMP-3, MMP-8, MMP-9 and MMP-13. MMP-2 is implicated in primary tumor growth as well as in tumor metastasis. This particular MMP is able to digest collagen and other ECM proteins as a precondition for cancer invasion and metastasis.

Although a great deal of effort is being directed to design and testing of anti-cancer agents, there is a continuing need for a non-toxic therapeutic agent that can effectively block MMP-mediated digestion of ECM, thereby attenuating the spread of cancer and other diseases.

SUMMARY OF THE INVENTION

An object of the present invention is to provide a synthetic oligopeptide having an amino acid sequence analogous to specific amino sequence of the matrix metalloproteinase 2 sequence (85-92) that is effective in blocking cancer invasion and cancer metastasis.

Another object of the present invention is to provide a synthetic oligopeptide consisting essentially of the amino acid sequence shown in SEQ. ID. No. 2. Preferably, the synthetic oligopeptide has a therapeutic concentration range between about 1 µM to about 500 µM. More preferably, the synthetic oligopeptide has a therapeutic concentration range between about 50 µM to about 200 µM. The synthetic oligopeptide may have a modified C-terminal end or a modified N-terminal end. Preferably, the synthetic oligopeptide is repeated. More preferably, synthetic oligopeptide is dipeptide or tripeptide.

Another object of the present invention is to provide a pharmaceutical composition comprising a synthetic oligopeptide which consists essentially of the amino acid sequence shown in SEQ. ID. No. 2, and a pharmaceutical acceptable carrier. Preferably, the pharmaceutical composition comprising the synthetic oligopeptide has a therapeutic concentration range of between about 1 µM to about 500 µM. More preferably, the synthetic oligopeptide has a therapeutic concentration range of between about 50 µM to about 200 µM. Preferably, the pharmaceutical composition comprising the synthetic oligopeptide has a modified C-terminal end or a modified N-terminal end.

Preferably, the pharmaceutical composition comprises the synthetic oligopeptide which is repeated. More preferably, the synthetic oligopeptide is dipeptide or tripeptide.

Another object of the invention is to provide a pharmaceutical composition comprising a synthetic oligopeptide useful in treating a cancer metastasis selected from the group of brain cancer, lung cancer, skin cancer, and breast cancer.

Another object of the invention is to provide a method for treating cancer invasion and metastasis comprising the step of administering to a human patient suffering from cancer a therapeutically effective amount of a synthetic oligopeptide which consists essentially of the amino acid sequence shown in SEQ.ID. No. 2.

Preferably, the cancer metastasis is selected from the group of brain cancer, lung cancer, skin cancer, and breast cancer.

BRIEF DESCRIPTION OF THE DRAWINGS

Sequences II-VII are SEQ. ID. Nos. 2-7, respectively. Sequence Ref is SEQ. ID. No. 8.

DETAILED DESCRIPTION OF THE INVENTION

Definitions: As used herein, the term "peptide" refers to an organic compound comprising two or more amino acids covalently joined by peptide bonds; a peptide may be a dipeptide (which contains two peptides having the repeated amino acid residues), or a tripeptide (which contains three peptides having the repeated amino acid residues).

As used herein, the term "oligopeptide" refers to a peptide that is typically less than 30 residues in length. The length of oligopeptides is not critical to the invention so long as the correct epitope is maintained. Desirably, the oligopeptide can be as small as possible while still maintaining substantially all the biological activity of the large oligopeptide and remaining effective in blocking cancer cell invasion and metastasis.

"Oligopeptide" is used interchangeably with "synthetic peptide" in this application. The oligopeptide used in this invention is an 'isolated" but "biologically pure" synthetic peptide.

"Therapeutic" means an agent utilized to treat, combat, ameliorate, prevent or improve a disease condition in a patient. "Therapeutic amount" of an agent refers to an amount of the agent effective in treating, combating, ameliorating, preventing or improving a disease condition. A particular condition treated in the present invention is the malfunctioning of MMP associated with cancer metastasis. Accordingly, therapeutic treatment of MMP disorders may have implications in diseases including cancer metastasis, including brain cancer, lung cancer, skin cancer and breast cancer.

As used herein, the one-letter symbols for amino acid residues are: A (alanine); R (arginine); N (asparagine); D (aspartic acid); C (cysteine); Q (glutamine); E (glutamic acid); G (glycine); H (histidine); I (isoleucine); L (leucine); K (lysine); M (methionine); F (phenylalanine); P (proline); S (serine); T (threonine); V (valine); W (tryptophan); and Y (tyrosine).

Amino acid substitutions are typically of single residues. Substitutions, deletions, insertions or any combination thereof may be combined to arrive at an oligopeptide. Conserved amino acid substitutions consist of replacing one or more amino acids with amino acids with similar charge, size and/or hydrophilicity characteristics, such as, for example, a glutamic acid (E) to aspartic acid (D) amino acid subsitution. Non-conserved substitutions consist of replacing one or more amino acids with amino acids possessing dissimilar charge, size, and/or hydrophilicity, such as, for example, a glutamic acid (E) to valine (V) substitution. The present invention is intended to encompass conservative changes of oligopeptide with respect to substitutions, deletions, insertions or any combination thereof so long as the effectiveness of blocking cancer cell invasion and metatstasis is substantially unchanged.

Rath et al. (J Applied Nutr. 44:62-69, 1992; J Orthomolecular Med. 8:11-20, 1993) have postulated that oligopeptide that oligopeptides maxima conformation and electric charge mediate pathogenesis of a multitude of diseases. According to the postulation, a selected sequence of amino acid in the MMP enzyme may block the action of the enzyme by attaching itself to the complimentary sequence in the substrate. This concept is entirely different than the one detailed by Liotta et al. (U.S. Pat. No. 5,372,809) in which the oligopeptide blocks the zinc molecule in the enzyme. The experimental evidence indicating that complexes of different types of protein in the cells can modify the activity of the proteins in the cell (Gavin and Associates, Nature 415:141-147, 2002) is in essence confirmation of the postulate. The references cited herein are incorporated by reference in their entirety.

In the present invention, we identified possible oligopeptide sequences in the amino acid sequence of MMP-2 and found that these oligopeptide sequences effectively interfere with the functional activity of MMP-2 using in vitro invasion of ECM by cancer cells as test model.

Without being limited by theory of mechanism or actions, the present invention provides oligopeptides that can effectively block cancer cell invasion and metastasis. One mechanism of action may be that MMP-2 binds to the target ECM molecules via specific binding sites. Blocking these binding sites may therefore prevents MMP-2 from binding to its ECM substrate molecules, inhibits the destruction of the ECM and thereby prevents cancer and other diseases from spreading throughout the body. Several potential binding sites within the MMP-2 protein have been identified, the present invention provides that synthetic analogs to these oligopeptides sequences are effective to prevent ECM destruction. One of the therapeutic oligopeptides is PRKPKWDK (SEQ. ID. No. 2), which is shown to inhibit the invasion of cancer cells by about 90%.

The present invention additionally provides a therapeutic use of the oligopeptide in other MMP-related diseases. Because MMP-2 may use the same sites to bind to its target molecules within the ECM, the oligopeptide disclosed in the present invention can similarly interfere other diseases. Thus, the preventive and therapeutic use of the synthetic oligopeptides claimed here are not limited to cancer but can also be used in cardiovascular disease and other pathological conditions associated with the destruction of the ECM by MMPs. These oligopeptides can be applied to a patient as a vaccine.

The present invention embodies synthetic peptides effective in blocking cancer cell invasion. The benefits of these agents and the antibodies to them are the utility in clinical applications for preventing and treating cancer invasion and metastasis. Preferably, synthetic oligopeptides which have the amino acid of SEQ ID. 2 are useful in blocking cancer invasion and metastasis. More preferably, the synthetic peptides are included in a pharmaceutical formulation for blocking cancer invasion and metastasis.

The oligopeptide may be composed of about 6 to about 20 residues. Most preferably, the oligopeptide is composed of about 8 to about 10 residues. Most preferably, the synthetic oligopeptide contains 8 amino acid residues in length.

Preferably, the concentration of synthetic peptides ranges from 1 µM to 500 µM. Most preferably, the concentration of synthetic peptides ranges from 50 µM to 200 µM.

Another object of the present invention is to use the synthetic peptides as an immunogen to generate antibodies so that such generated antibodies can effectively block cancer invasion and metastasis. Preferably, the synthetic oligopeptide contains 8 amino acid residues in length.

Another object of the present invention is an immunogenic oligopeptide that is included in pharmaceutical composition comprising a pharmaceutically acceptable carrier and the oligopeptides. The oligopeptide can be used as a vaccine. The pharmaceutical composition comprising oligopeptide can be used to induce an immune response against a protein comprising an eptiope having the sequence of the oligopeptide (e.g., SEQ. ID. 2).

The present invention provides a synthetic oligopeptide having amino acid sequence analogous to an amino acid sequence within the protein of human MMP-2.

The amino-and/or carboxy-termini of the synthetic oligopeptide can comprise an amino group (—NH$_2$) or a carboxy (—COOH) group, respectively. Alternatively, the oligopeptide amino-terminus may, for example, represent a hydrophobic group, including but not limited to carbobenzyl, dansyl, t-butoxycarbonyl, decanyl, napthyl or other carbohydrate group; an acetyl group; 9-florenymethoxy-carbonyl (FMOC) group; or a modified, non-naturally occurring amino acid residue. Alternatively, the synthetic oligopeptide carboxy-terminus can, for example, represent an amino group; a t-butoxycarbonyl group; or a modified non-naturally occurring amino acid residue. Alternatively, the present invention encompasses synthetic oligopeptides that block cancer cell invasion and metastasis by omitting an amino residue at the N-terminal end or the C-terminal end. The present invention also provides a modification of oligopeptides that block cancer cell invasion and metastasis by substituting an amino acid residue within the given sequence without consideration of charge and polarity of the substitution residue.

It is to be understood that the present invention also contemplates peptide analogues wherein one or more amide linkage is optionally replaced with a linkage other than amide, preferably a substituted amide or an isostere of amide. Thus, while the amino acid residues within peptides are generally described in terms of amino acids, and preferred embodiments of the invention are exemplified by way of peptides, one having skill in the art will recognize that in embodiments having non-amide linkages, the term "amino acid" or "residue" as used herein refers to other bifunctional moieties bearing groups similar in structure to the side chains of the amino acids. In addition the amino acid residues may be blocked or unblocked.

The present invention provides a modification of oligopeptides that block cancer cell invasion and metastasis by repeating the oligopeptide sequence, each of them covalently bound to one or more oligopeptide repeat(s).

The present invention provides a preventive or therapeutic use of one or more of the oligopeptides to directly and competitively reduce or block the metabolic action or interaction of MMP-2 by intravenous application or in another therapeutically acceptable way.

The present invention provides a preventive or therapeutic use of one or more of the oligopeptides to indirectly reduce or block the metabolic action or interaction of MMPs by applying them as vaccines by subcutaneous application or in another acceptable manner to stimulate a specific immune response which can partially or completely block the metabolic interaction of MMPs. A preferred embodiment includes MMP-2.

The present invention provides a preventive and therapeutic use of one or more of the oligopeptides where the oligopeptides are coupled to haptens to enhance immune response and thereby therapeutic efficacy.

The present invention provides a preventive or therapeutic use of one or more of the oligopeptides to function as feedback regulators to specifically prevent or reduce the synthesis rate of MMP-2 proteins at the cellular level.

The present invention provides one of more oligopeptides that block cancer cell invasion and metastasis as a vaccine for the production of specific antibodies for the diagnosis of a disease involving MMP-2 or the clinical monitoring of the progression or regression of this disease.

The present invention provides the use of one or more oligopeptides that block human disease, including, but not limited to cancer cell invasion and metastasis for the prevention or therapy of cancer disease, infectious disease, cardiovascular disease and degenerative disease.

The present invention provides the use of one or more of oligopeptides that block cancer cell invasion and metastasis for the prevention or therapy of diseases involving MMP-2.

The present invention provides the use of one or more of oligopeptides that block cancer cell invasion and metastasis. These oligopeptides can be applied to a patient type, injection, infusion, inhalation, suppository or other pharmaceutically acceptable carrier and/or means of delivery. The method of administering peptides and formulations of the present invention may employ any of a number of known administrative routes such as oral, IV, subcutaneous, transcutaneous and topical administration. A preferred method of the present invention employs a pharmaceutical composition for parenteral administration.

Compositions of the present invention may be in the form of a peptide or peptides in combination with at least one other agent, such as a stabilizing compound, which may be administered in any sterile, bio-compatible pharmaceutical carrier, including, but not limited to, saline, buffered saline, dextrose, and water. The compositions may be administered to a patient singly, or in combination with other agents, drugs or hormones. Pharmaceutically-acceptable carriers may also be comprised of excipients and auxiliaries which facilitate processing of the active compounds into preparations which can be used pharmaceutically. Further details on techniques for formulation and administration may be found in the latest edition of "Remington's Pharmaceutical Sciences", Mack Publishing Co., Easton, Pa., which technologies are incorporated by reference in their entirety. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms.

The oligopeptides of the present invention can also be used as vaccines to raise antibodies for assays used to diagnose diseases involving MMPs (in particular, MMP-2) as well as the clinical monitoring of the progression or regression of disease through blood assays or in other suitable diagnostic assays.

The following examples are intended as illustrations of the practice of this invention and are not meant to limit the scope of the invention.

Oligopeptide Sequences

The amino acid sequence of MMP-2 regarding regions of high hydrophility maxima enriched with charged amino acids were identified with a software program. The oligopeptides of the present invention may be synthesized or prepared by techniques well known in the art. See, for example, Proteins: Structures and Molecular Principles, Creighton, W. H. Freeman and Co., N.Y. (1983) which is incorporated herein by reference in its entirety. The oligopeptides prepared and used in the present invention are listed in Table 1.

The inhibitory effects of these oligopeptides on the MATRIGEL™ invasion and migration through the MATRIGEL™ membrane by various cancer cells were evaluated using "Improved MATRIGEL™ Invasion Chamber" (Becton Dickinson, USA). The oligopeptide TMRKPRCGNPDVAN (SEQ. ID. No. 8) which was shown to have anti-MMP-2 activity by Liotta and Associates was used as a standard reference for oligopeptides.

TABLE 1

Various Oligopeptide Sequences Identified and Used In the Studies

| Oligopeptide | Sequence Number |
| --- | --- |
| GDVAPKTDKE | SEQ. ID. 1 |
| PRKPKWDK | SEQ. ID. 2 |
| EDYDRDKKY | SEQ. ID. 3 |
| GRSDGLM | SEQ. ID. 4 |
| NYDDDRKW | SEQ. ID. 5 |
| LPPDVQRVD | SEQ. ID. 6 |
| RYNEVKKKMDP | SEQ. ID. 7 |
| TMRKPRCGNPDVAN | SEQ. ID. 8 |

General Experimental Conditions

The identified oligopeptides were custom synthesized. They were then used for MATRIGEL™ invasion studies.

(a) MATRIGEL™ Invasion Studies

The studies were conducted using "Improved MATRIGEL™ Invasion Chambers" (Becton Dickinson, USA).

In studies with human melanoma cells, human fibroblasts-NHDF (Clonetics) were seeded on MATRIGEL™ inserts and allowed to reach confluence. This was done to closely simulate in vivo conditions surrounding cancer cells in the body.

Human melanoma cells A2058 were then seeded on the insert. Conditioned media from the fibroblast culture supplemented with various levels of chosen oligopeptide were added to the chamber. The system was incubated for about 24 hours. At the end of the period the cells on the upper surface of the insert were wiped off. The cells that had invaded the MATRIGEL™ membrane and had migrated to the lower surface of the insert were stained with "quick stain" and were counted under the microscope. The percent inhibition was calculated by the number of cells that failed to migrate through the membrane as compared to control ("0" level of oligopeptide). The inhibitory activity of the control was considered as "0". The media from invasion assays were saved for zymogram studies.

In studies with human breast cancer cells MCF7 the procedure was essentially similar to that used for melanoma cells, except that MRC5 (ATCC) fibroblasts were used in place of NHDF.

In studies with human breast cancer cells MDA-MB 231 the fibroblast-MRC5 cells were plated in the wells. The rest of the procedure remained the same as in studies with MCF7 cells.

(b) Zymogram Studies

The media (25-30 μl) from various wells in invasion studies were applied to NOVEX® zymogram gels (Invitrogen). The gels were developed and stained as recommended by the manufacturer. The matrix metalloproteinases (MMPs) were identified on the basis of their known molecular weights.

EXAMPLE 1

Inhibitory effects of various oligopeptide sequences on MATRIGEL™ Invasion and migration by melanoma cells A2058

Figure 1:
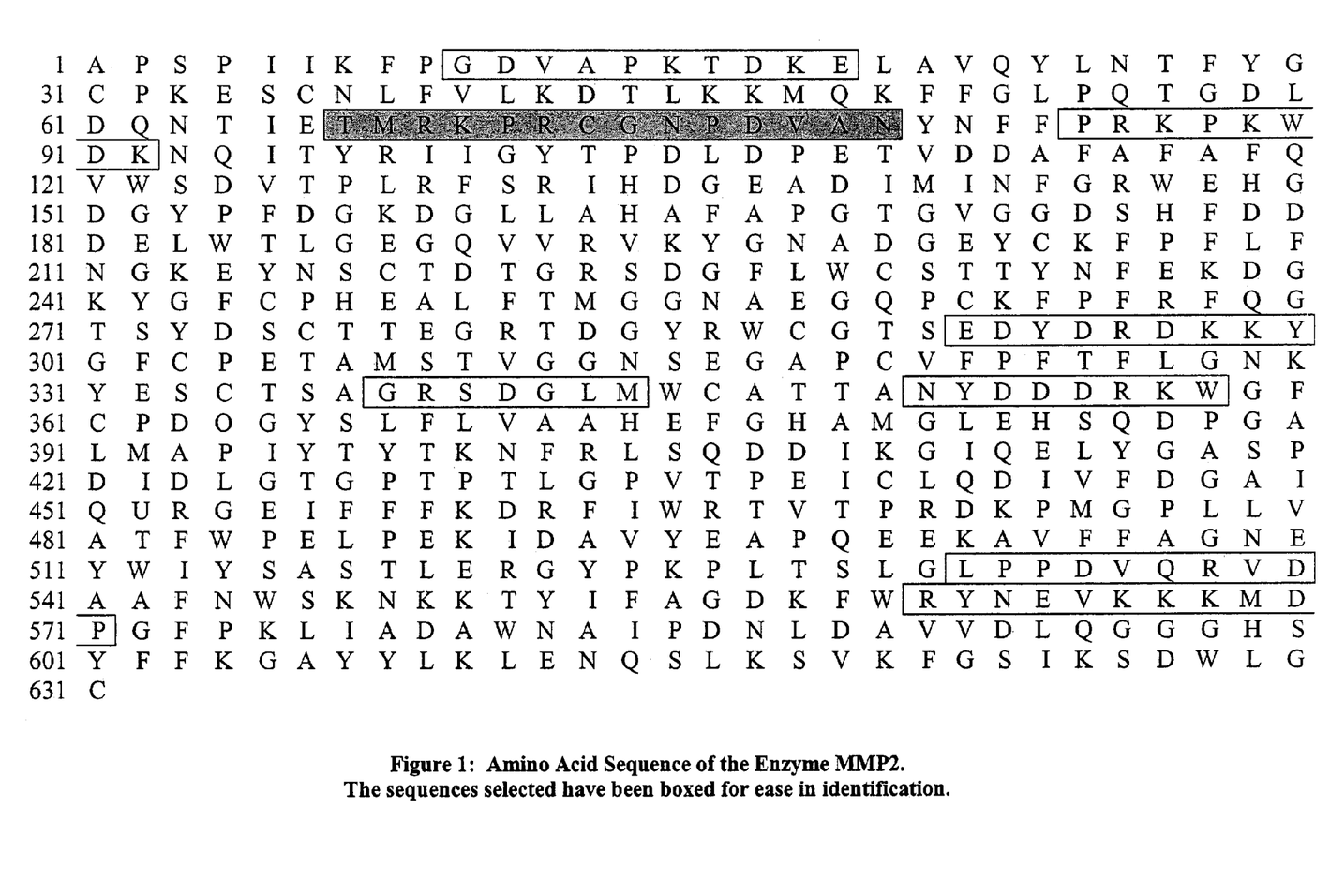
FIG. 1 depicts the amino acid sequence of the human MMP-2 enzyme. The boxed, unshaded sequences are SEQ. ID. Nos. 1-7, respectively. The boxed, shaded sequence is SEQ. ID. No. 8, which is used as a reference.

FIG. 1 depicts the amino acid sequences selected for inhibitory activity studies have been boxed for easy identification. The amino acid sequence TMRKPRCGNPDVAN (SEQ. ID. No. 8) (also boxed) which has been demonstrated to inhibit the activity of MMP2 (Loitta et. al.) was used a reference.

Figure 2:
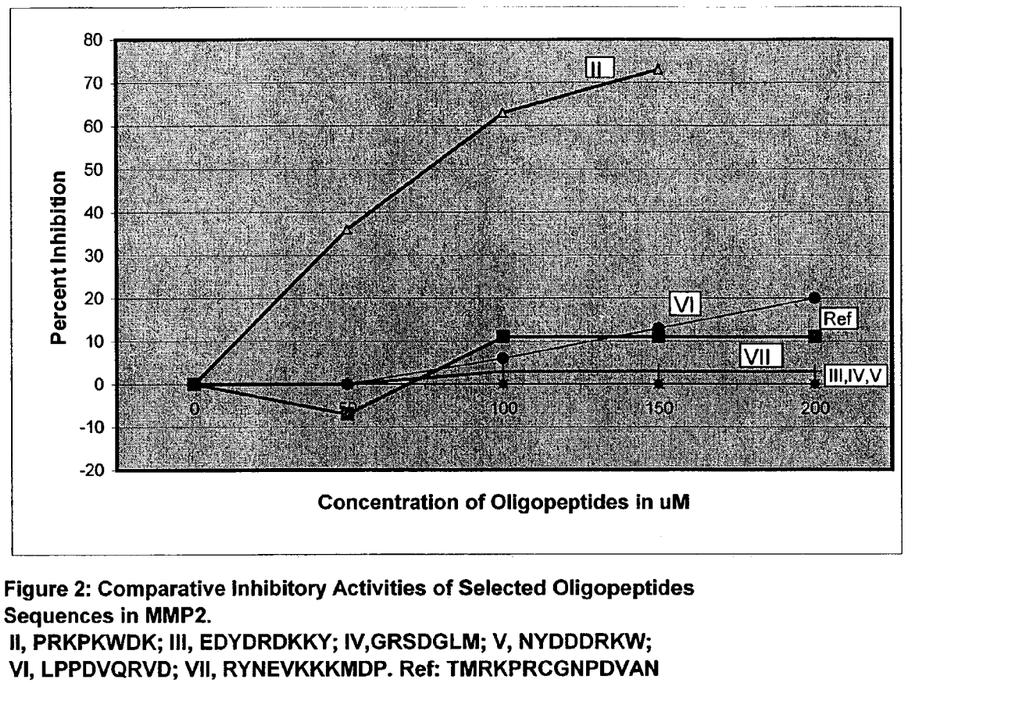
FIG. 2 depicts the comparative inhibitory effects of various oligopeptides tested.

Seven (7) oligopeptides (see Table 1 for their amino acid sequences) were tested for inhibiting invasion of human melanoma cancer cells. Oligopeptide having the amino acid sequence PRKPKWDK (SEQ. ID. No. 2) showed blocking activity. Oligopeptide having TMRKPRCGNPDVAN (SEQ. ID. No. 8) showed about 11% inhibition as compared to 73% shown by PRKPKWDK (SEQ. ID. No. 2) (FIG. 2).

Oligopeptide VI having the amino acid sequence LPPDVQRVD (SEQ. ID. No. 6) also had some blocking activity (i.e., about 20%). Oligopeptide "I" having the amino acid sequence GDVAPKTDKE (SEQ. ID. No. 8) did not show any activity up to 100 μM concentration (not shown in FIG. 2), as against 63% shown by PRKPKWDK (SEQ. ID. No. 2) at the same concentration.

EXAMPLE 2

Inhibitory effects of oligopeptide PRKPKWDK (SEQ. ID. No. 2) on MATRIGEL™ Invasion and migration by melanoma cells A2058

In these studies the concentration of PRKPKWDK (SEQ. ID. No. 2) in the medium was varied between 0 to 150 μM. It was seen that the oligopeptide progressively inhibited the invasion by the melanoma cells (FIG. 3) from about 37% at 50 .mu.M concentration to 73% at 150 μM.

Figure 3:
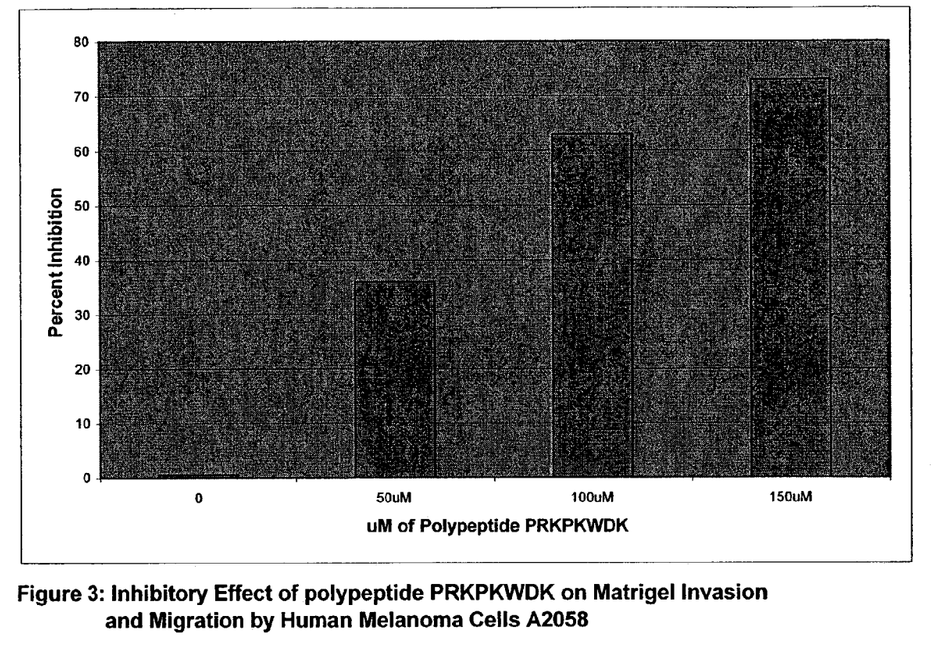
FIG. 3 depicts an inhibition of an oligopeptide having the amino acid sequence of PRKPKWDK (SEQ. ID. No. 2) in blocking cancer cell invasion using MATRIGEL™ basement membrane matrix assay with human melanoma cancer cells A2058.

These data show that oligopeptide having the amino acid sequence of PRKPKWDK (SEQ. ID. No. 2) is highly effective in blocking cancer cell invasion using MATRIGEL™ assay with human melanoma cancer cells A2058.

The MATRIGEL™ membrane is analogous to ECM and the ability of cancer cells to break through and migrate to the other side of the membrane represents the ability of the cancer cells to metastasize in the body. The oligopeptide was able to significantly reduce invasion of three different types of cancer cells. In this test system the activity was directed against ECM. It is concluded that the oligopeptide can interfere with degradation of ECM in the body and thereby adversely affect the progression of diseases in which breakdown of ECM is the basic mechanism.

EXAMPLE 3

Figure 4:
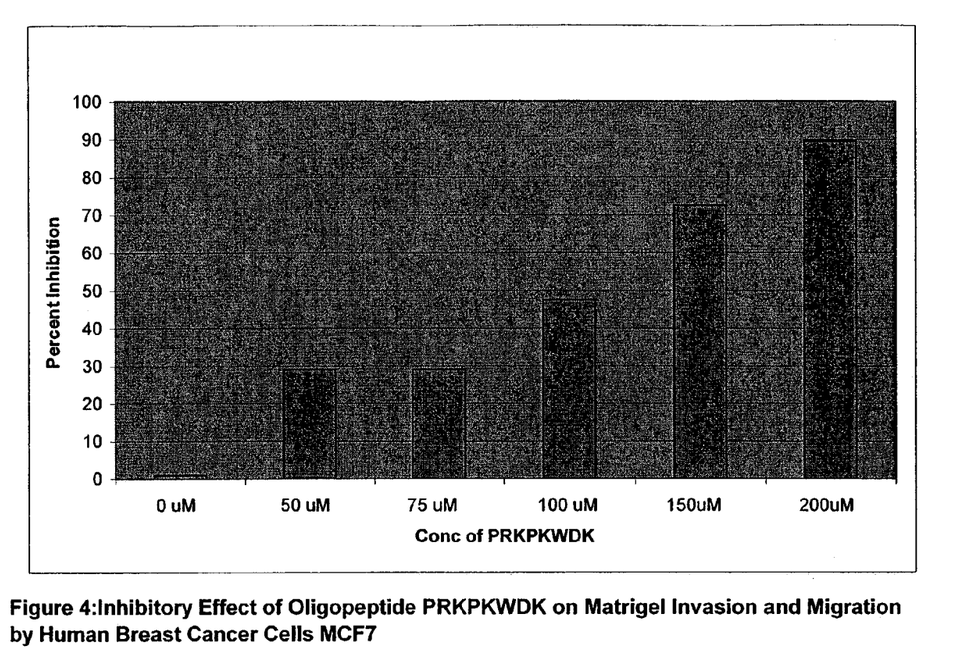
FIG. 4 depicts an inhibition of an oligopeptide having the amino acid sequence of PRKPKWDK (SEQ. ID. No. 2) in blocking cancer cell invasion using MATRIGEL™ assay with human breast cancer cells MCF7.

In these studies we determined the inhibitory effects of PRKPKWDK (SEQ. ID. No. 2) on the MATRIGEL™ invasion and migration by human breast cancer cells MCF7 (ATCC). As with melanoma cells this oligopeptide inhibited the cancer cell invasion. The inhibition at 150 μM concentration was about 70%. It increased to about 90% at 200 μM concentration (FIG. 4).

EXAMPLE 4

In these studies we investigated the inhibitory activity of PRKPKWDK (SEQ. ID. No. 2) with human breast cancer cells-MDA-MB 231. The inhibition at 150 μM concentration was found to be about 94%.

EXAMPLE 5

We next assessed if the oligopeptides can interfere with the action of the enzyme after it was secreted. Zymogram studies did not show any inhibitory effect of the PRKPKWDK (SEQ. ID. No. 2) on the amount of MMP-2 secreted by the cancer cells used in this study.

While the foregoing has been set forth in considerable detail, the sequences are presented for elucidation, and not limitation. Modifications and improvements, including equivalents, of the technology disclosed above which are within the purview and abilities of those in the art are included within the scope of the claims appended hereto. It will be readily apparent to those skilled in the art that numerous modifications, alterations and changes can be made with respect to the details of the above description without departing from the inventive concept described herein. For example, modification (either chemical or enzymatic) of the basic sequences described herein is also within the purview of the present invention. For example, the disclosed sequence can be a dipeptide or tripeptide. The disclosed sequences may also be modified to include this residue at either the amino or carboxyl ends of the peptides. The sequences may also be chemically modified to increase their activity (e.g., amidation of the carboxyl terminus portion of a sequence). The peptides may be chemically modified to increase their activity (e.g., amidation of the carboxy terminus portion of a sequence or including a glycine or alanine residue at either end).

Accordingly, it is understood that various modifications may be made without departing from the spirit and scope of the present invention as set forth in the claims below.

What is claimed is:

1. A method for inhibiting invasion of human melanoma cells or human breast cancer cells, comprising treating the human cells with an effective amount of a synthetic oligopeptide where the synthetic oligopeptide is less than 30 residues in length and consists essentially of the amino acid sequence as set forth in SEQ. ID. No. 2.

2. A method for inhibiting invasion of melanoma cells or breast cancer cells in a human patient, comprising treating said human patient by administering to the patient a pharmaceutical composition comprising an effective amount of a synthetic oligopeptide where the synthetic oligopeptide is less than 30 residues in length and consists essentially of the amino acid sequence shown in SEQ. ID. No. 2, and a pharmaceutical acceptable carrier.

* * * * *

SEQUENCE LISTING

<160> NUMBER OF SEQ ID NOS: 8

<210> SEQ ID NO 1
<211> LENGTH: 10
<212> TYPE: PRT
<213> ORGANISM: Homo sapiens

<400> SEQUENCE: 1

Gly Asp Val Ala Pro Lys Thr Asp Lys Glu
1               5                   10

<210> SEQ ID NO 2
<211> LENGTH: 8
<212> TYPE: PRT
<213> ORGANISM: Homo sapiens

<400> SEQUENCE: 2

Pro Arg Lys Pro Lys Trp Asp Lys
1               5

<210> SEQ ID NO 3
<211> LENGTH: 9
<212> TYPE: PRT
<213> ORGANISM: Homo sapiens

<400> SEQUENCE: 3

Glu Asp Tyr Asp Arg Asp Lys Lys Tyr
1               5

<210> SEQ ID NO 4
<211> LENGTH: 7
<212> TYPE: PRT
<213> ORGANISM: Homo sapiens

<400> SEQUENCE: 4

Gly Arg Ser Asp Gly Leu Met
1               5

<210> SEQ ID NO 5
<211> LENGTH: 8
<212> TYPE: PRT
<213> ORGANISM: Homo sapiens

<400> SEQUENCE: 5

Asn Tyr Asp Asp Asp Arg Lys Trp
1               5

<210> SEQ ID NO 6
<211> LENGTH: 9
<212> TYPE: PRT
<213> ORGANISM: Homo sapiens

<400> SEQUENCE: 6

Leu Pro Pro Asp Val Gln Arg Val Asp
1               5

<210> SEQ ID NO 7
<211> LENGTH: 11
<212> TYPE: PRT
<213> ORGANISM: Homo sapiens

<400> SEQUENCE: 7

Arg Tyr Asn Glu Val Lys Lys Lys Met Asp Pro
1               5                   10

```
<210> SEQ ID NO 8
<211> LENGTH: 14
<212> TYPE: PRT
<213> ORGANISM: Homo sapiens

<400> SEQUENCE: 8

Thr Met Arg Lys Pro Arg Cys Gly Asn Pro Asp Val Ala Asn
1               5                   10
```